US012039721B2

(12) United States Patent
Sawkey

(10) Patent No.: US 12,039,721 B2
(45) Date of Patent: Jul. 16, 2024

(54) CLASSIFICATION OF ORGAN OF INTEREST SHAPES FOR AUTOSEGMENTATION QUALITY ASSURANCE

(71) Applicant: Siemens Healthineers International AG, Steinhausen (CH)

(72) Inventor: Daren Sawkey, Palo Alto, CA (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 515 days.

(21) Appl. No.: 17/362,657

(22) Filed: Jun. 29, 2021

(65) Prior Publication Data

US 2022/0414867 A1 Dec. 29, 2022

(51) Int. Cl.
*G06T 7/12* (2017.01)
*G06F 18/214* (2023.01)
(Continued)

(52) U.S. Cl.
CPC ........ *G06T 7/0012* (2013.01); *G06F 18/2148* (2023.01); *G06F 18/22* (2023.01);
(Continued)

(58) Field of Classification Search
CPC .................. G06T 7/0012; G06T 7/174; G06T 2207/20084; G06T 2207/30016;
(Continued)

(56) References Cited

U.S. PATENT DOCUMENTS 9,757,589 B2 9/2017 Zankowski
10,675,486 B2 6/2020 Toimela et al.
(Continued)

OTHER PUBLICATIONS

Chen Xinyuan et al.: "CNN-Based Quality Assurance for Automatic Segmentation of Breast Cancer in Radiotherapy", Frontiers in Oncology, vol. 10, Apr. 28, 2020 (Apr. 28, 2020), XP055966689, CH ISSN: 2234-943X, DOI: 10.3389/fonc.2020.00524 abstract.

(Continued)

*Primary Examiner* — Charlotte M Baker
(74) *Attorney, Agent, or Firm* — FOLEY & LARDNER LLP

(57) ABSTRACT

Embodiments described herein provide for receiving a second image comprising an overlay depicting an organ-at-risk (OAR) segmentations. The overlay is generated by a first machine learning model based on a first image depicting the anatomical region of a current patient. A second machine learning model receives the second image and set of third images depicting prior patient OAR segmentations on which the second machine learning model was trained. The second machine learning model classifies the second image as one of a set of class names and characterizes the extent to which the second image is similar to, or dissimilar to, images with the same class name in the set of third images. The characterization may be based on outputs of internal layers of the second machine learning model. Dimensionality reduction may be performed on the outputs of the internal layers to present the outputs in a form comprehendible by humans.

20 Claims, 10 Drawing Sheets

(51) Int. Cl.
| | |
|---|---|
| G06F 18/22 | (2023.01) |
| G06F 18/2411 | (2023.01) |
| G06N 20/00 | (2019.01) |
| G06T 7/00 | (2017.01) |
| G06T 7/174 | (2017.01) |
| G06V 10/44 | (2022.01) |
| G16H 30/20 | (2018.01) |
| A61B 5/055 | (2006.01) |
| A61B 6/03 | (2006.01) |
| A61B 8/08 | (2006.01) |

(52) U.S. Cl.
CPC ......... *G06F 18/2411* (2023.01); *G06N 20/00* (2019.01); *G06T 7/174* (2017.01); *G06V 10/44* (2022.01); *G16H 30/20* (2018.01); *A61B 5/055* (2013.01); *A61B 6/032* (2013.01); *A61B 6/037* (2013.01); *A61B 8/08* (2013.01); *G06T 2207/20084* (2013.01); *G06T 2207/30016* (2013.01); *G06T 2207/30168* (2013.01); *G06V 2201/031* (2022.01)

(58) Field of Classification Search
CPC . G06T 2207/30168; G06T 2207/20081; G06T 2207/30004; G06T 7/10; G06F 18/2148; G06F 18/22; G06F 18/2411; G06N 20/00; G06V 10/44; G06V 2201/031; G16H 30/20; A61B 5/055; A61B 6/032; A61B 6/037; A61B 8/08
USPC ...................................................... 382/128
See application file for complete search history.

(56) References Cited

U.S. PATENT DOCUMENTS

| | | |
|---|---|---|
| 2012/0027271 A1 | 2/2012 | Zankowski |
| 2018/0235563 A1* | 8/2018 | Nam .................... A61B 8/5238 |

OTHER PUBLICATIONS

Ho Hin Lee et al.: "Semi-Supervised Multi-Organ Segmentation through Quality Assurance Supervision", arxiv.org, Cornell University Library, 201 Olin Library Cornell University Ithaca, NY 14853, Nov. 12, 2019 (Nov. 12, 2019), XP081531338.
International Search Report and Written Opinion on PCT Appl. Ser. No. PCT/US2022/034452 dated Oct. 11, 2022 (15 pages).
Li Ke et al.: "Quality Assurance using Outlier Detection on an Automatic Segmentation Method for the Cerebellar Pedunces", Feb. 2, 2016 (Feb. 2, 2016), XP055965884, Retrieved from the Internet: URL:http://iac1.ece.jhu.edu/proceedings/ia c1/2016/ LixSPIE16-Quality_Assurance.pdf [retrieved on Sep. 28, 2022] abstract.
Nix M et al.: "PH-0606: AutoConfidence: Per-patient validation for clinical confidence in deep learning for radiotherapy", Radiotherapy and Oncology, Elsevier, Ireland; vol. 152, Nov. 1, 2020 (Nov. 1, 2020), XP086490569, ISSN: 0167-8140, DOI: 10.1016/S0167-8140(21)00628-9 [retrieved on Feb. 5, 2021].
Brie Goo, Katrina May, Haobo Zhang, James Olivas; "Machine Learning Solution to Organ-At-Risk Segmentation for Radiation Treatment Planning;" Santa Clara University, Interdisciplinary Design Senior Theses; Jun. 13, 2019; 41 pages.
Carlos E Cardenas, Jinzhong Yang, Brian M Anderson, Laurence E Court, Kristy B Brock; "Advances in Auto-Segmentation;" Semin Radiat Oncol. Jul. 2019: 185-197; Jul. 2019, 13 pages.
Chenjie Ge, Irene Yu-Hua Gu, Asgeir Store Jakola, Jie Yang; "Deep semi-supervised learning for brain tumor classification"; BMC Medical Imaging vol. 20; Jul. 29, 2020; 11 pages.
Ehsan Adeli; Kim-Han Thung; Le An; Guorong Wu; Feng Shi; Tao Wang; Dinggang Shen; "Semi-Supervised Discriminative Classification Robust to Sample-Outliers and Feature-Noises;" IEEE Transactions on Pattern Analysis and Machine Intelligence, vol. 41, Issue 2; Feb. 1, 2019; 8 pages.
F. Vaassen, C. Hazelaar, A. Vaniqui, M. Gooding, B. van der Heyden, R. Canters, W. V. van Elmpt; "Evaluation of measures for assessing time-saving of automatic organ-at-risk segmentation in radiotherapy;" Physics and Imaging in Radiation Oncology, vol. 13, pp. 1-6; Jan. 2020; 6 pages.
Gregory Sharp, Karl D Fritscher, Vladimir Pekar, Marta Peroni, Nadya Shusharina, Harini Veeraraghavan, Jinzhong Yang; "Vision 20-20_Perspectives on automated image segmentation for radiotherapy;" published online Med Phys. May 2014; 41(5): 050902; Apr. 24, 2014; 13 pages.
Haradhan Chel, P K Bora; "Novel Outlier Detection Based Approach to Registering Pre- and Post-resection Ultrasound Brain Tumor Images;" 2017 4th International Conference on Advances in Electrical Engineering (ICAEE); Sep. 2017; 7 pages.
Luca Biasiolli, Qiang Zhang, Iulia A. Popescu, Konrad Werys, Elena Lukaschuk, Valentina Carapella, Jose M. Paiva, Nay Aung, Jennifer J. Rayner, Kenneth Fung, Henrike Puchta. Mihir M. Sanghvi, Niall O. Moon, Katharine E. Thomas; "Quality Control-Driven Image Segmentation Towards Reliable Automatic Image Analysis in Large-Scale Cardiovascular Magnetic Resonance Aortic Cine Imaging;" Lecture Notes in Computer Science (LNCS, vol. 11765); Oct. 10, 2019; 9 pages.
Head-Neck-Radiomics-HN1, DOI: 10.7937/tcia.2019.8kap372n, Jul. 29, 2020.

* cited by examiner

CLASSIFICATION OF ORGAN OF INTEREST SHAPES FOR AUTOSEGMENTATION QUALITY ASSURANCE

TECHNICAL FIELD

This application relates generally to using artificial intelligence modeling to classify organ shapes for autosegmentation quality assurance.

BACKGROUND

Radiotherapy (radiation-based therapy) is used as a cancer treatment to emit high doses of radiation that can kill cells or shrink a tumor. The goal is to deliver enough radiation to a target region of the patient's anatomy to kill the cancerous cells during the radiotherapy treatment. However, other organs or anatomical regions that are close to, or surrounding, the target region can be in the way of radiation beams and can receive enough radiation to damage or harm such organs or anatomical regions. These organs or anatomical regions are referred to as organs at risk ("OARs" or "OAR" for a single organ at risk). Typically a physician or a radiation oncologist identifies both the target region and the OARs prior to radiotherapy using various imaging modalities. Furthermore, simulation images of the patient's anatomy may be obtained.

For safe and effective radiotherapy treatment, it is crucial to accurately segment OARs to minimize radiation exposure to these healthy tissues. Due to rapid advances in radiation therapy such as image guidance and treatment adaptation, a fast and accurate segmentation of medical images is a very important part of the treatment. Manual delineation of target volumes and organs at risk is still standard routine for many clinics, even though it is time consuming and prone to intra-observer and inter-observer variations. Automated segmentation methods seek to reduce delineation workload and unify the organ boundary definition. Clinical applications can benefit from automated image segmentation and achieve not only efficient image segmentation but also improved consistency and objectivity for diagnosis.

In deploying automated segmentation to clinical applications, however, it is necessary to address the issue of quality control. Conventional autosegmentation methods, even those that incorporate machine learning, can still fail. It is important to detect any critical inaccuracies, which can lead to misidentification. Current clinical practice of segmentation quality control may require human visual inspection, e.g., by a radiation oncologist. Relying on human visual inspection as a standard practice diminishes the benefits of efficiency brought forth by automated segmentation. This poses a need to integrate automated quality control in image analysis pipelines to efficiently and reliably extract clinical parameters.

SUMMARY

For the aforementioned reasons, there is a need for systems and methods for classification of OAR shapes and shapes of other organs of interest for autosegmentation quality assurance over a range of human anatomy. There is a need for autosegmentation of organs of interest at an accuracy similar to a radiation oncologist, while still providing for segmentation of organs of interest via human visual inspection for selected patients. Discussed herein are systems and methods that integrate automated quality control methods to identify appropriate cases for manual delineation of OARs. Disclosed systems and methods can characterize the distribution of training data, and detect outliers in training data and in inference-time predictions. Embodiments described herein may compute accuracy metrics of inference-time predictions. Also, the embodiments described herein may assist clinicians in visualizing classification results.

In various embodiments, the method integrates automated quality control techniques to identify cases not appropriate for automatic delineation of OARs. The method receives a second image comprising a first overlay predicting a segmentation of a structure of an anatomical region of a patient, wherein the first overlay may be generated by a first machine learning model. The second image may include at least one OAR segmentation for a current patient. In some embodiments, the method also receives a first image representing a medical image of the anatomical region depicting the structure of the current patient.

The method executes a second machine learning model, trained on a set of third images that classifies the second image and characterizes the similarity between the second image and the set of third images. Training data for the second machine learning model may include a set of organ segmentations for prior patients. The second machine learning model inputs the second image for the current patient to determine the classification of the second image. The layer outputs of the second machine learning model with the second image and the set of third images are output by the model. These outputs are used to determine whether the first overlay generated by the first machine learning model is outside the distribution of the third images.

The method may generate 1D, 2D, or 3D visual representation of the second image and of the set of third images. The second machine learning model may categorize the second image as similar to, or dissimilar to, the set of third images. The method may include the step of displaying one or both of the visual representation and the categorization of the second image on an electronic device. The method may include the step of transmitting a notification instructing a manual review of the second image in the event the second machine learning model determines that the first overlay generated by the first machine learning model is outside the distribution of the training data.

In an embodiment, the second machine learning model classifies the second image as one of a predefined set of class names. The set of third images represent segmentations of organs of prior patients of the same class name as the second image, and a set of fourth images represent segmentations of organs of prior patients of a different class name than the second image. In this embodiment, the set of third images and the set of fourth images are both used to train the second machine learning model.

The second machine learning model may be a deep learning model including one or more of neural networks, convolutional neural networks, residual neural networks, random forest, and support vector machines. The second machine learning model may be trained via an unsupervised training protocol. The reliability classification may correspond to a weight of a neural network layer of the second machine learning model. The second machine learning model may be configured to perform dimensional reduction on model inputs via one or more dimensionality reduction techniques including principal component analysis (PCA) and t-distributed stochastic neighbor embedding (t-SNE), among others. The second machine learning model may be configured to normalize spatial attributes other than shape of the set of second structures of the set of third images. The second machine learning model may be configured to generate a one-dimensional plot, a two-dimensional plot, or a three-dimensional plot in which each of the second structures is represented a respective point. The second machine learning model may be configured to identify an attribute of a patient associated with at least one third image corresponding to at least one outlier shape.

In an embodiment, a method comprises receiving, by the processor, a second image comprising a first overlay predicting a segmentation of an organ of a patient, wherein the first overlay is generated by a first machine learning model using a first image depicting an anatomical region of the patient including the organ; and executing, by the processor, a second machine learning model that receives the second image to classify similarity between the second image and a set of third images representing a set of second structures by characterizing the extent to which the second image is drawn from a distribution of images in a plurality of images within the set of third images; wherein the set of third images representing the set of second structures is used to train the second machine learning model.

The second machine learning model may be configured to identify at least one cluster of second structures represented by the set of third images.

The distribution of images in the plurality of images may comprise a distribution of images of at least one cluster of second structures represented by the set of third images.

The second machine learning model may be further configured to identify at least one outlier second structure within the set of second structures represented by the set of third images.

The second machine learning model may be configured to classify the similarity between the second image and the set of third images representing the set of second structures by indicating whether or not the second image is drawn from the same distribution of images as the plurality of images within the set of third images.

The method may further include displaying, by the processor, the classifying the similarity between the second image and the set of third images representing the set of second structures by indicating whether or not a contour of the second image is drawn from the same distribution of contours as the plurality of images within the set of third images.

In the event of classifying the second image as not drawn from the same distribution of images as the plurality of images within the set of third images, further comprising displaying, by the processor, an attribute of a patient associated with the classification.

In the event of classifying the second image as not drawn from the same distribution of images as the plurality of images within the set of third images, the method may further comprise transmitting, by the processor, a notification instructing a manual review of the second image.

The second machine learning model may be a deep learning model comprising one or more of neural networks, convolutional neural networks, residual neural networks, random forest, and support vector machines.

The second machine learning model may be configured to perform dimensional reduction on model inputs via one or both of principal component analysis (PCA) and t-distributed stochastic neighbor embedding (t-SNE).

The method may further include receiving, by the processor, the first image depicting an anatomical region of the patient including the organ.

The first image may be one or more of an X-ray image, computed tomography (CT) image, magnetic resonance imaging (MM) image, positron emission tomography (PET) image, or ultrasound image.

The second machine learning model may be configured to generate one or more of a one-dimensional plot in which each of the second structures of the set of third images is represented by a respective point, a two-dimensional plot in which each of the second structures of the set of third images is represented by a respective point, and a three-dimensional plot in which each of the second structures of the set of third images is represented by a respective point.

In an embodiment, a method comprises receiving, by the processor, a second image comprising a first overlay predicting a segmentation of an organ of a patient, wherein the first overlay is generated by a first machine learning model using a first image depicting an anatomical region of the patient including the organ; and executing, by the processor, a second machine learning model that receives the second image to classify the second image as one of a predefined set of class names, and to classify similarity between the second image and a set of third images, wherein the set of third images represent segmentations of organs of prior patients of the same class name as the second image, wherein a set of fourth images represent segmentations of organs of prior patients of a different class name than the second image, wherein the set of third images and the set of fourth images are used to train the second machine learning model.

The predefined set of class names may represent a curated selection of organs based upon an anatomy of interest.

In an embodiment, a system comprises a server comprising a processor and a non-transitory computer-readable medium containing instructions that when executed by the processor causes the processor to perform operations comprising: receive a second image comprising a first overlay predicting a segmentation of an organ of a patient, wherein the first overlay is generated by a first machine learning model using a first image depicting an anatomical region of the patient including the organ; and execute a second machine learning model that receives the second image to classify similarity between the second image and a set of third images representing a set of second structures by characterizing the extent to which the second image is drawn from a distribution of images in a plurality of images within the set of third images; wherein the set of third images representing the set of second structures is used to train the second machine learning model.

The processor may further be configured to perform operations comprising: identify at least one cluster of second structures represented by the set of third images, wherein the distribution of images in the plurality of images comprises a distribution of images of at least one cluster of second structures represented by the set of third images.

The processor may further be configured to perform operations comprising: classify the similarity between the second image and the set of third images representing the set of second structures by indicating whether or not the second image is drawn from the same distribution of images as the plurality of images within the set of third images; and in the event of classifying the second image as not drawn from the same distribution of images as the plurality of images within the set of third images, further comprising transmitting, by the processor, a notification instructing a manual review of the second image.

The second machine learning model may be a deep learning model comprising one or more of neural networks, convolutional neural networks, residual neural networks, random forest, and support vector machines; wherein the second machine learning model is trained via an unsupervised training protocol.

The processor may further be configured to perform operations comprising: execute the second machine learning model that receives the second image to classify the second image as one of a predefined set of class names, and to classify similarity between the second image and a set of third images, wherein the set of third images represent segmentations of organs of prior patients of the same class name as the second image, wherein a set of fourth images represent segmentations of organs of prior patients of a different class name than the second image, wherein the set of third images and the set of fourth images are used to train the second machine learning model.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
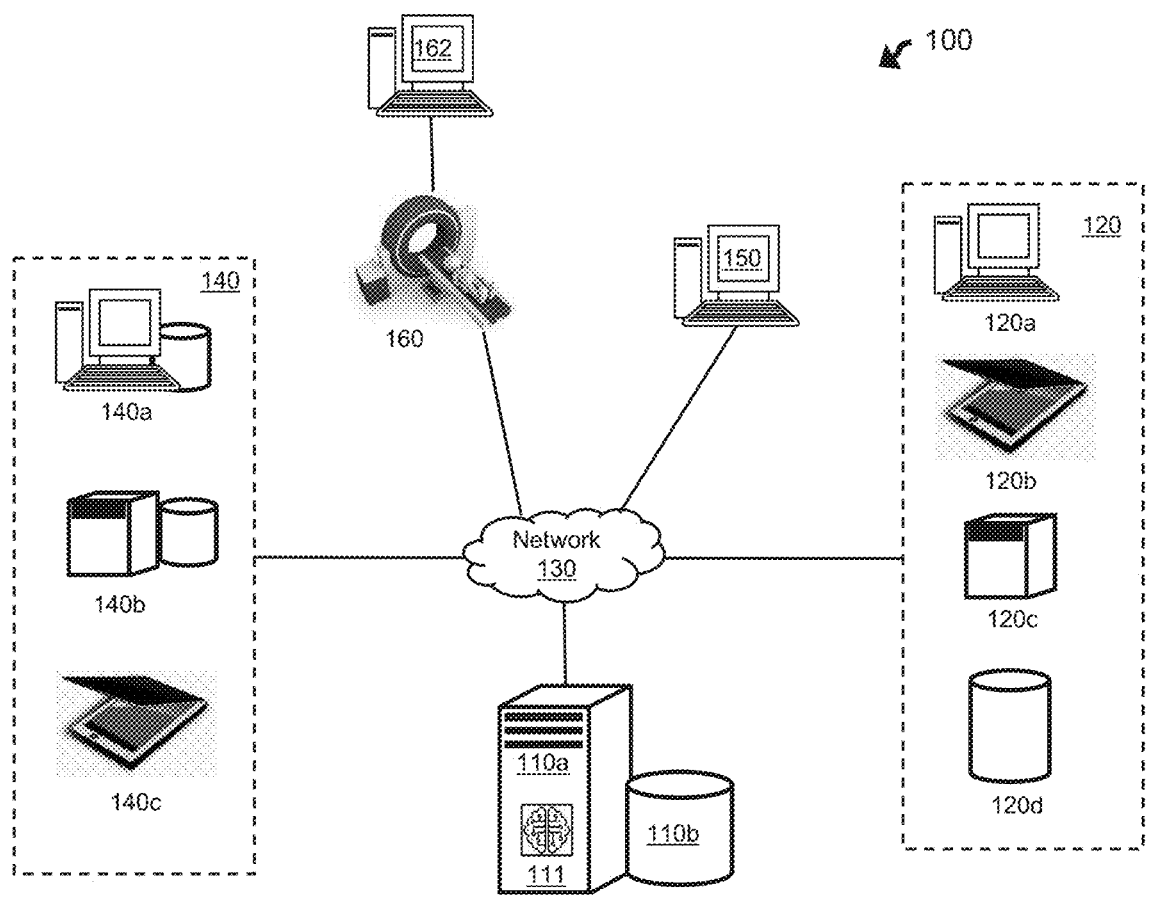
FIG. 1 illustrates components of a system for autosegmentation quality assurance, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

When medical imaging is necessary to observe an internal organ or a set of internal organs, there are several systems that may be utilized such as X-ray, computed tomography (CT), cone beam CT images (CBCT), four-dimensional CT images (e.g., CT images over time), magnetic resonance imaging (MRI) images, positron emission tomography (PET) images, ultrasound images, and or a combination thereof. When CT or MRI imagery, for example, is used, a series of two-dimensional images are taken from a three-dimensional volume. Here, each two-dimensional image is an image of a cross-sectional "slice" of the three-dimensional volume. The resulting collection of two-dimensional cross-sectional slices can be combined to create a three dimensional image or reconstruction of the patient's anatomy. This resulting three-dimensional image or three-dimensional reconstruction will contain the desired internal organ. This portion of the three-dimensional image or reconstruction that contains the structure of interest may be referred to as a volume of interest.

One purpose of the three-dimensional reconstruction of the structure(s) of interest containing diseased or abnormal tissues or organs is the preparation of a radiation therapy treatment plan. To verify that a radiation treatment procedure is correctly applied, quality assurance protocols are implemented to verify that the developed treatment plan is accurate.

Radiation therapy treatment plans are used during medical procedures that selectively expose precise areas of the body, such as cancerous tumors, to specific doses of radiation to destroy the undesirable tissues. An initial treatment plan may be prepared that defines the area in the human body to be treated, such as cancerous tissue, abnormal cells, lesions, and organs, called the clinical target volume (CTV). Another volume called the planning target volume (PTV) allows for uncertainties in planning or treatment delivery to ensure that the radiotherapy dose is actually delivered to the CTV. Radiotherapy planning generally considers critical normal tissue structures near the CTV, known as organs at risk. The goal is to deliver enough radiation to the PTV to kill the cancerous cells during the radiotherapy treatment. OARs that are close to, or surrounding, the PTV can be in the way of radiation beams and can receive enough radiation to damage or harm such organs or anatomical regions. Usually a physician or a radiation oncologist identifies both the PTV and the OARs prior to radiotherapy using a suitable imaging modality. Furthermore, simulation images of the patient's anatomy may be obtained.

For safe and effective radiotherapy treatment, it may be crucial to accurately segment OARs to minimize radiation exposure to these healthy tissues. Manual segmentation methods rely on delineation of OARs, while automated segmentation methods may be deployed to reduce delineation workload. In deploying automated segmentation to clinical applications it is necessary to address the issue of quality control. State-of-the-art autosegmentation methods such as methods incorporating machine learning can still fail, such as in cases affected by poor image quality, pathologies, or natural variations in anatomy. Quality assurance may require human visual inspection by a physician or radiation oncologist, but relying on manual inspection as a standard practice diminishes the benefits of efficiency brought forth by automated segmentation. Disclosed embodiments integrate automated quality control methods to identify appropriate cases for manual delineation of OARs, while relying on automated segmentation of OARs or other target volumes in cases in which automated methods are determined to have an accuracy similar to a radiation oncologist.

FIG. 1 illustrates components of a system for autosegmentation quality assurance 100, according to an embodiment. The system 100 may include an analytics server 110a, system database 110b, machine learning models 111, electronic data sources 120a-d (collectively electronic data sources 120), end-user devices 140a-c (collectively end-user devices 140), an administrator computing device 150, and a medical device 160 having a medical device computer 162. Various components depicted in FIG. 1 may belong to a radiotherapy clinic at which patients may receive radiotherapy treatment, in some cases via one or more radiotherapy machines located within the clinic (e.g., medical device 160). The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The system 100 is not confined to the components described herein and may include additional or other components, not shown for brevity, which are to be considered within the scope of the embodiments described herein.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), or EDGE (Enhanced Data for Global Evolution) network.

The analytics server 110a may generate and display an electronic platform configured to use various computer models 111 (including artificial intelligence and/or machine learning models) for autosegmentation quality assurance. More specifically, at an inference phase for a patient treatment plan, the electronic platform may display a reliability classification indicative of an accuracy of medical images containing autosegmentation contours of a current patient's OARs or other target volumes. The electronic platform may display one or more medical images such as images of patient OARs or other internal organs, and images of autosegmentation contours of such organs. Depending on reliability classification, the platform may transmit a notification instructing a manual quality assurance review of the autosegmentation medical images. The electronic platform may include a graphical user interface (GUI) displayed on each electronic data source 120, the end-user devices 140, and/or the administrator computing device 150. An example of the electronic platform generated and hosted by the analytics server 110a may be a web-based application or a website configured to be displayed on different electronic devices, such as mobile devices, tablets, personal computer, and the like.

Additionally, the electronic platform may display two-dimensional and/or three-dimensional quality assurance plots output by the artificial intelligence models 111 based upon autosegmentation contours of prior patient medical images and the current patient's medical images. In cases in which the current patient's autosegmentation images are determined to represent an outlier in comparison to a regular distribution of prior patient autosegmentation images, the artificial intelligence models 111 may identify one or more patient attributes associated with the outlier determination.

In a non-limiting example, a physician or radiation oncologist operating the medical professional device 120b, 140c may access the platform, review the reliability classification and medical images, and in appropriate cases may initiate a manual quality assurance review. The physician or radiation oncologist may visually inspect two-dimensional and/or three-dimensional quality assurance plots based upon autosegmentation contours of prior patient and current patient medical images. The physician or radiation oncologist may compare data distribution of plot elements corresponding to prior patient medical images with one or more plot elements for the patient in treatment. Additionally, the physician or radiation oncologist may review one or more attributes identified by the machine learning model 111 in cases in which the patient's autosegmentation images are determined to represent an outlier in comparison to a regular distribution of segmentations (autosegmentation images). Therefore, the medical professional devices (e.g., the medical professional device 140c) may be used as both a device to display results predicted by the analytics server 110a and in some cases used as an electronic data source (e.g., electronic data source 120b) to train the machine learning model 111.

The analytics server 110a may host a website accessible to users operating any of the electronic devices described herein (e.g., end users, medical professionals), where the content presented via the various webpages may be controlled based upon each particular user's role or viewing permissions. The analytics server 110a may be any computing device comprising a processor and non-transitory machine-readable storage capable of executing the various tasks and processes described herein. The analytics server 110a may employ various processors such as central processing units (CPU) and graphics processing unit (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with displayed content.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g., LDAP). The analytics server 110a may generate webpage content that is customized according to the user's role defined by the user record in the system database 110b.

The analytics server 110a may receive medical images from a user or retrieve such data from a data repository, analyze the data, and display the results on the electronic platform. For instance, in a non-limiting example, the analytics server 110a may query and retrieve medical images from the database 120d and combine the medical images with segment data received from a physician operating the medical professional device 120b. Additionally, or alternatively, the analytics server 110a may segment the medical image automatically or perform other pre-processing steps on the medical image captured from the medical device 160.

The analytics server 110a may execute various machine learning models 111 (e.g., stored within the system database 110b) to analyze the retrieved data. The analytics server 110a may then display the results via the electronic platform on the administrator computing device 150 and/or the end-user devices 140.

The electronic data sources 120 may represent various electronic data sources that contain, retrieve, and/or input data associated with a patient's treatment plan including patient data and treatment data. For instance, the analytics server 110a may use the clinic computer 120a, medical professional device 120b, server 120c (associated with a physician and/or clinic), and database 120d (associated with the physician and/or the clinic) to retrieve/receive data associated with the patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110a. Specifically, the end-user devices 140 may include clinic computer 140a, clinic server 140b, and a medical processional device 140c. Even though referred to herein as "end user" devices, these devices may not always be operated by end users. For instance, the clinic server 140b may not be directly used by an end user. However, the results stored onto the clinic server 140b may be used to populate various GUIs accessed by an end user via the medical professional device 140c.

The administrator computing device 150 may represent a computing device operated by a system administrator. The administrator computing device 150 may be configured to display radiation therapy treatment attributes generated by the analytics server 110a (e.g., various analytic metrics determined during training of one or more machine learning models and/or systems); monitor various models 111 utilized by the analytics server 110a, electronic data sources 120, and/or end-user devices 140; review feedback; and/or facilitate training or retraining (calibration) of the machine learning models 111 that are maintained by the analytics server 110a.

The medical device 160 may be a radiotherapy machine configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include a stereo systems (e.g., two systems may be arranged orthogonally). The medical device 160 may also be in communication with a medical device computer 162 that is configured to display various GUIs discussed herein. For instance, the analytics server 110a may display the results predicted by the machine learning model 111 onto the medical device computer 162.

In operation, a physician or other medical professional may access an application executing on the medical professional device 120b and input patient data and the patient's treatment data (e.g., patient information, patient diagnosis, radiation therapy radiation requirements and thresholds). The analytics server 110a then uses a patient identifier to query patient data (e.g., patient anatomy and/or medical images) from the electronic data sources 120. The analytics server may then identify a clinic associated with the patient (e.g., clinic performing the treatment) and retrieve one or more files associated with treatment templates and clinic rules. The analytics server 110a may then utilize the systems and methods described herein to generate autosegmentation quality assurance data.

A medical professional at a radiotherapy clinic may access an end-user device 140 located at the clinic or access an account associated with the clinic. The medical professional may provide an input at a user interface that causes the end user device 140 to transmit a request to access a machine learning model 111 that is associated with the clinic and/or the radiotherapy machines located within the clinic. The request may include an identifier associated with the machine learning model 111, the clinic, a treatment plan generated by the one or more medical professionals, and/or the set of radiotherapy machines that the analytics server 110a may use as a key in a look-up table to identify the machine learning model 111. The analytics server 110a may receive the request and, in some cases, after authenticating the user, identify the machine learning model 111 via the identifier. The analytics server 110a may transmit the identified machine learning model 111 to the end-user device 140 or send an alert indicating the end-user device is authorized to access the model(s) 111. Upon receipt or access to the machine learning model 111, the end user device 140 may perform the systems and methods described herein to train or retrain the machine learning model 111 to predict autosegmentation quality assurance data.

The analytics server 110a may store machine learning models 111 (e.g., neural networks, random forest, support vector machines, or other deep learning models), that are trained to predict the anatomical structure represented by various pixels or voxels of a medical image. Various machine learning techniques may involve "training" the machine learning models to predict (e.g., estimate the likelihood of) each pixel or voxel of a medical image being associated with or otherwise representing a particular anatomical structure.

A first machine learning model 111 may be trained to generate an overlay predicting a contour of an anatomical region of a first patient depicting a structure such as an OAR, e.g., at inference time for a patient treatment plan. A second machine learning model 111 may be trained to receive medical images of the anatomical region of the patient depicting a structure and the overlay predicting a contour of the anatomical region. The second machine learning model may identify at least one outlier shape within a set of second structures, such as OARs or other structures displayed in medical images of prior patients. The second machine learning model may be configured to categorize the contour of the anatomical region of the first patient as similar to, or dissimilar to, a set of third images in training data based on the degree of similarity of the contour of the anatomical region and the at least one outlier shape. The second machine learning model may be configured to output one-dimensional, two-dimensional and/or three-dimensional plots in which the structure contour for each patient is represented by a point or other image element. Such two-dimensional and/or three-dimensional plot may facilitate detecting outlier shapes, either visually or algorithmically.

Machine learning models 111 may be stored in the system database 110b and may correspond to individual radiotherapy clinics or otherwise different sets of radiotherapy machines (e.g., radiotherapy machines that are located at individual radiotherapy clinics, are located in different geographical regions, treat specific types of diseases (e.g., different types of cancer), treat specific genders, etc.). For example, the machine learning model 111 may be associated with an identifier indicating the radiotherapy clinic, set of radiotherapy machines, or a specific disease.

In various embodiments, machine learning models 111 use one or more deep learning engines to perform automatic segmentation of image data for radiotherapy treatment planning. Although exemplified using deep convolutional neural networks, it should be understood that any alternative and/or additional deep learning model(s) may be used to implement deep learning engines. The deep learning engines include processing pathways that are trained during training phase. Once trained, deep learning engines may be used (e.g., by a clinician) to perform automatic segmentation for current patients during inference phase.

One type of deep learning engine is a convolutional neural network (CNN). A CNN is a branch of neural networks and consists of a stack of layers each performing a specific operation, e.g., convolution, pooling, loss calculation, etc. Each intermediate layer receives the output of the previous layer as its input. The beginning layer is an input layer, which is directly connected to an input image and may have a number of neurons equal to the number of pixels in the input image. The next set of layers are convolutional layers that present the results of convolving a certain number of filters with the input data and perform as a feature extractor. The filters, commonly known as kernels, are of arbitrary sizes defined by designers depending on the kernel size. Each neuron responds only to a specific area of the previous layer, called receptive field. The output of each convolution layer is considered as an activation map, which highlights the effect of applying a specific filter on the input. Convolutional layers may be followed by activation layers to apply non-linearity to the activation maps. The next layer can be a pooling layer that helps to reduce the dimensionality of the convolution's output. In various implementations, high-level abstractions are extracted by fully connected layers. The weights of neural connections and the kernels may be continuously optimized in the training phase.

A computer can be provided with a large dataset and, by using deep learning algorithms, can sort elements of the data into categories such as function, shape, etc. A "clustering" may occur based on similarity of data.

The aim of training phase is to train a deep learning engine to perform automatic classification of input segmentation data, by mapping the input data (segmentation data) to example output data (labels). Training phase may involve finding weights that minimize the training error between training label data, and estimated label data generated by deep learning engine. During training phase, the deep learning engine may be trained using suitable training data relating to automatic segmentation of OARs. In practice, training data may include segmented image data for patient OARs as example input data, and labels or class names as output data. Structure data may identify any suitable contour, shape, size and/or location of structure(s) or segment(s) of a patient's anatomy. A 3D volume of the patient that will be subjected to radiation is known as a treatment volume, which may be divided into multiple smaller volume-pixels (voxels).

In practice, training data may be user-generated through observations and experience to facilitate supervised learning. For example, training data may be extracted from past treatment plans developed for prior patients. Training data may be pre-processed via any suitable data augmentation approach (e.g., rotation, flipping, translation, scaling, noise addition, cropping, any combination thereof, etc.) to produce a new dataset with modified properties to improve model generalization using ground truth.

Figure 2:
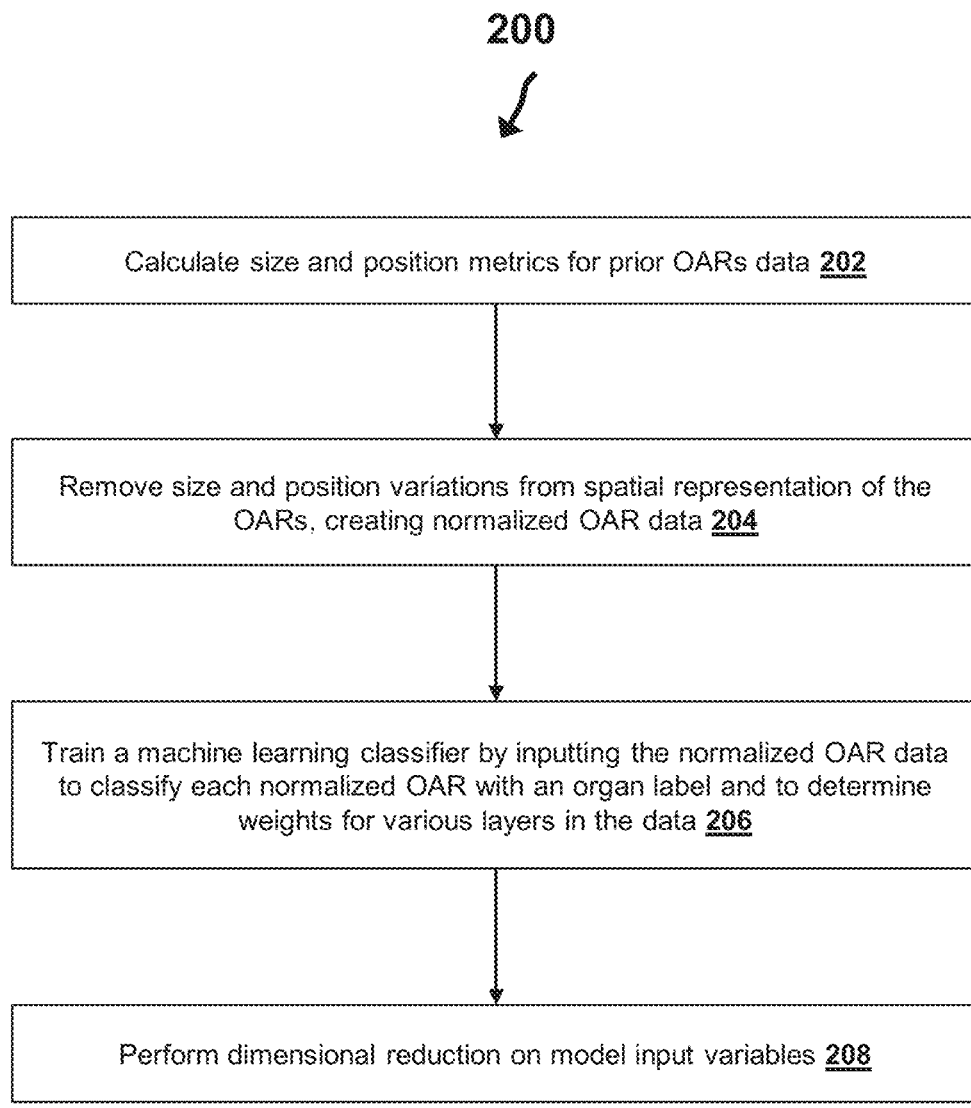
FIG. 2 illustrates a flow diagram of a process for characterizing shapes of prior patient segmentations to train a machine learning model, according to an embodiment.

FIG. 2 illustrates a flow diagram of a process executed in autosegmentation quality assurance, according to an embodiment. The method 200 includes steps for characterizing the shapes or contours of OARs in a set of prior patient OAR segmentation images and for training a machine learning model. In another process, the trained machine learning model can be used at inference time in quality assurance assessment of current patient OAR segmentation images. The method 200 may include steps 202-206. However, other embodiments may include additional or alternative steps, or may omit one or more steps altogether.

The method 200 is described as being executed by an analytics server, such as the analytics server described in FIG. 1. The analytics server may employ one or more processing units, including but not limited to CPUs, GPUs, or TPUs, to perform one or more steps of method 200. The CPUs, GPUs, and/or TPUs may be employed in part by the analytics server and in part by one or more other servers and/or computing devices. The servers and/or computing devices employing the processing units may be local and/or remote (or some combination). For example, one or more virtual machines in a cloud may employ one or more processing units, or a hybrid processing unit implementation, to perform one or more steps of method 200. However, one or more steps of method 200 may be executed by any number of computing devices operating in the distributed computing system described in FIG. 1. For instance, one or more computing devices may locally perform part or all of the steps described in FIG. 2.

In characterizing an organ at risk or structure, spatial attributes may include size, relative position, orientation, and shape. Shape is generally most challenging to characterize. The process 200 normalizes spatial attributes other than shape in order to facilitate characterizing shape. In step 202, the analytics server calculates size and position metrics for a set of prior patent OAR medical images. These calculations may identify OARs that have anomalous size or position. In step 204, the analytics server removes size and position variations from spatial representation of the OARs, creating normalized OAR data. In an embodiment of step 204, the server normalizes the size, such as by setting the largest dimension of each OAR to the same dimensions, and discards the position data.

At step 206, the analytics server trains a machine learning classifier by inputting the normalized OARs into the classifier. In an embodiment, step 206 inputs a curated selection of prior patient OAR data based upon anatomy of interest. In an illustrative example, if the anatomy of interest is the uterus, the machine learning classifier may be trained via 20 OARs each of uterus, rectum, and bladder. At step 206, the classifier may classify each normalized OAR with an organ label and may include additional information in the weights for various layers of the machine learning model. This additional information can be useful, for example, in answering the question why the classifier identified a given OAR as a uterus.

At step 208, the analytic server performs dimensional reduction on model input variables. When employing deep learning models, each convolutional layer of the model may contains many input variables. In the present disclosure, dimensionality reduction refers to techniques for reducing the number of input variables in training data. Various disclosed embodiments employ one or more dimensionality reduction techniques, including principal component analysis (PCA) and t-distributed stochastic neighbor embedding (t-SNE), among others.

Principal component analysis (PCA) computes the principal components of a data set and uses them to perform a change of basis on the data, sometimes using only the first few principal components. Principal components are new variables that are constructed as linear combinations of the initial variables. In these combinations, the new variables are uncorrelated and most of the information within the initial variables is compressed into the first components. Principal component analysis can be employed as a feature selection algorithm that may provide data dimensionality reduction if needed. PCA can be applied to dimensionality reduction by projecting each data point onto only the first few principal components to obtain lower-dimensional data while preserving as much of the data's variation as possible.

t-distributed stochastic neighbor embedding (t-SNE) is a statistical method for visualizing high-dimensional data by giving each data point a location in a two or three-dimensional map. t-SNE constructs a probability distribution over pairs of high-dimensional objects such that similar objects are assigned a higher probability while dissimilar objects are assigned a lower probability. t-SNE then defines a similar probability distribution over the points in the low-dimensional map and it minimizes relative entropy between the two distributions with respect to the locations of the points in the map. t-SNE then defines a similar probability distribution over the points in the low-dimensional map and it minimizes relative entropy between the two distributions with respect to the locations of the points in the map. When t-SNE software constructs a map, it can provide better results than other dimensionality reduction methods such as principal components analysis (PCA) or classical multidimensional scaling. As compared with these other methods, t-SNE focuses primarily on modeling local structure in the map and t-SNE can correct for an enormous difference in volume of a high-dimensional feature space and a two-dimensional map.

Figure 3:
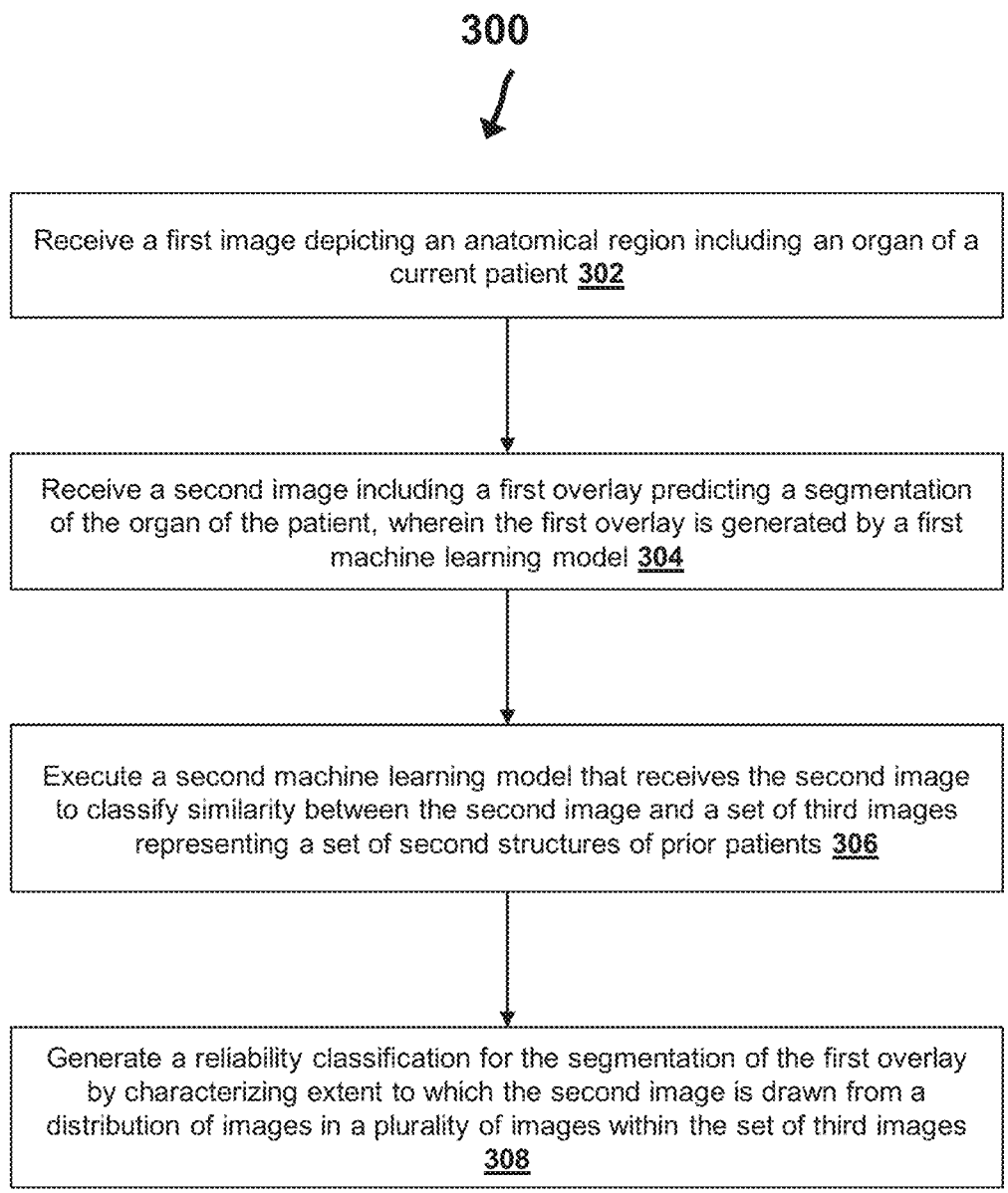
FIG. 3 illustrates a flow diagram of a process for predicting a contour of a current patient structure and generating a degree of similarity to training data indicating reliability of the contour, according to an embodiment.

FIG. 3 illustrates a flow diagram of a process executed in autosegmentation quality assurance, according to an embodiment. The method 300 generates an overlay by a first machine learning model predicting a contour of a current patient structure, and executes a second machine learning model which receives the overlay. The second machine learning model also receives a set of third images depicting prior patient OAR segmentations on which the second machine learning model was trained. The second machine learning model generates a reliability classification of the contour of the current patient structure by characterizing the extent to which the overlay is drawn from a distribution of images in a plurality of images within the set of third images.

In an embodiment, the second machine learning model classifies the overlay as one of a set of class names of the second machine learning model, and generates a reliability classification of the contour of the current patient structure based on a degree of similarity of the structure and the structures of the same OAR in the set of second structures. In an embodiment, a machine learning model trained by the method of FIG. 2 can be used at inference time as the second machine learning model in the process of FIG. 3. The method 300 may include steps 302-308. However, other embodiments may include additional or alternative steps, or may omit one or more steps altogether.

In step 302, the analytics server receives a first image depicting an anatomical region of the patient including an organ. In an embodiment, the analytical server receives the first image from a medical imaging system such as X-ray, computed tomography (CT), cone beam CT images (CBCT), four-dimensional CT images (e.g., CT images over time), magnetic resonance imaging (MRI) images, positron emission tomography (PET) images, ultrasound images, and or a combination thereof. In an embodiment, the first image includes an OAR organ or anatomical region. In an embodiment, step 302 is effected at inference phase for a current radiotherapy patient.

In step 304, the analytic server receives a second image including a first overlay predicting a contour of the structure, wherein the first overlay is generated by a first machine learning model. In an embodiment, the first machine learning model executes an autosegmentation algorithm to automatically segment an OAR. In an embodiment, the first machine learning model is operable to predict contours of OARs and other structures. In an embodiment, the first learning model is trained with a set of third images depicting a set of second structures. In an embodiment, the set of third images include prior patient medical images and the set of second structures include autosegmentation contours.

In an embodiment of method 300, the method omits the first step 302 of receiving the first image. In this case, in step 304 the second image including the first overlay received by the analytic server was previously generated by the first machine learning model using the first image comprising the anatomical region of the patient depicting the structure.

In step 306, the analytic server executes a second machine learning model that receives the second image to classify the second image and identify structures similar to the second image within a set of second structures of a set of third images. In an embodiment, the second machine learning model is a deep learning model such as neural networks (e.g., convolutional neural networks, residual neural networks), random forest, support vector machines, or other deep learning models. The second machine learning model may be trained via the method of FIG. 2. Step 306 may further include the step of normalizing the set of third images before the third images are transmitted to the second machine learning model.

The second machine learning model may apply dimensionality reduction, for example principal component analysis (PCA) or t-distributed stochastic neighbor embedding (t-SNE) to the set of second structures to generate one dimensional plots, two-dimensional plots, or three-dimensional plots in which each of the second structures is a point. The second machine learning model may apply a clustering analysis to group the set of second structures in at least one cluster. In addition to identifying one or more clusters of second structures, the second machine learning model may identify any outlier shapes.

In an embodiment, the second image includes at least one OAR model contour segmentation for a current patient, and the set of third images includes a set of prior patient OARs model contour segmentations. Step 306 applies the second machine learning model to the set of prior patient OAR segmentations together with at least one OAR model contour segmentation for the current patient. Model contour segmentations as used herein refers to machine learning model autosegmentation of structure shapes.

In step 308, the analytic server generates a reliability classification of the contour of the first overlay based on a degree of similarity of the structure and the cluster(s) identified at step 306. In an embodiment, the reliability classification may also be based on any outlier shape(s) identified at step 306. In an embodiment, the second machine learning model comprises a neural network and the degree of similarity of step 308 corresponds to a function of weights of the neural network.

In an embodiment of steps 306 and 308, the second machine learning model is configured to classify the second image as one of a predefined set of class names, and to classify similarity between the second image and a set of third images that represent segmentations of organs of prior patients of the same class name as the second image. In this embodiment, the set of third images and a set of fourth images are used to train the second machine learning model, wherein the set of fourth images represent segmentations of organs of prior patients of a different class name than the second image. The predefined set of class names may represent a curated selection of organs based upon an anatomy of interest.

In an embodiment, step 308 further includes displaying the reliability classification on an electronic device. Step 308 may present at least one of the first image or the second image for display on an electronic device. If the second machine learning model is configured to identify structures of a patient associated with at least one third image corresponding to at least one structure similar to the second image, step 308 may further include transmitting the attribute for display on an electronic device.

Step 308 may further include transmitting a notification instructing a manual review of the second image in the event the in the event the reliability classification indicates a low degree of similarity of the structure and the structures of the same OAR in the set of third images.

Step 308 may further include transmitting the first image and second image to a server, flagged to carry out a second level review of the second image.

Figure 4:
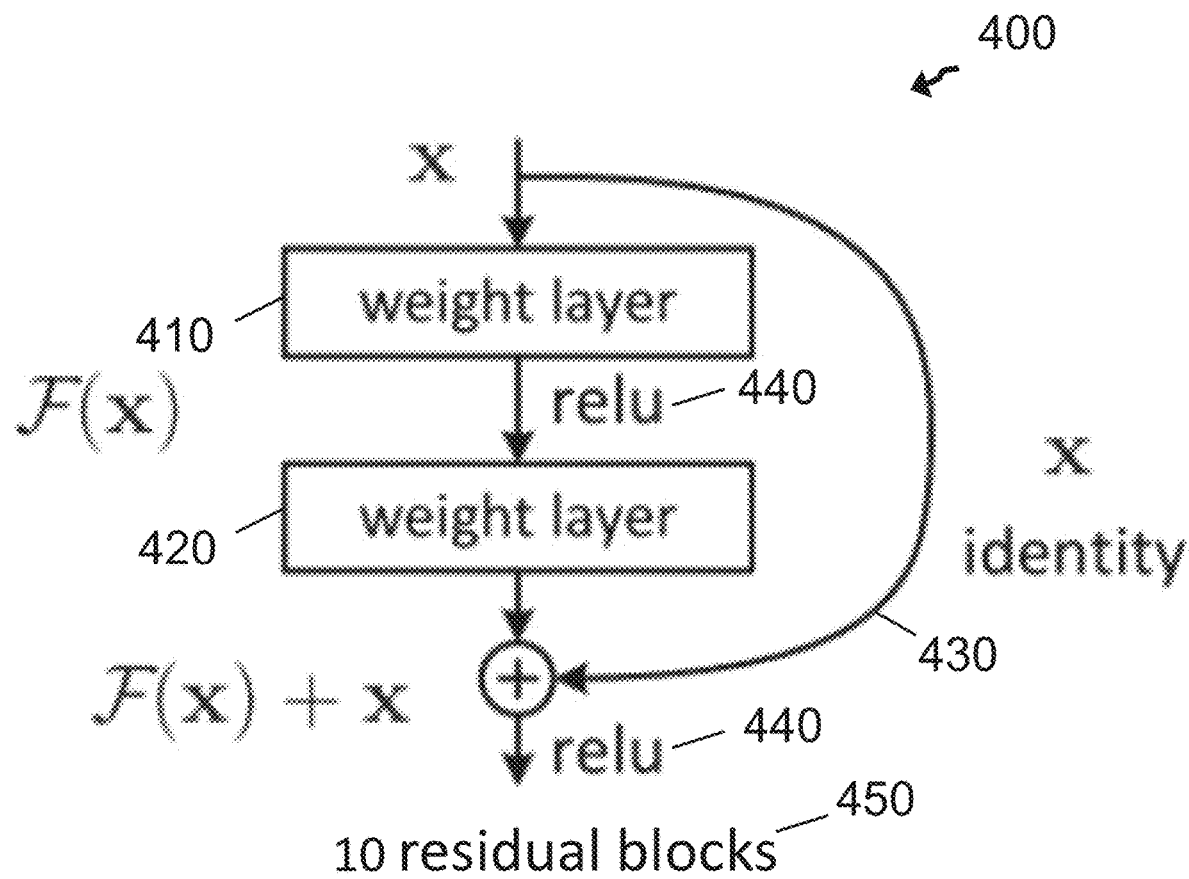
FIG. 4 illustrates an architecture of a 3D ResNet deep learning model, according to an embodiment.
Figure 5:
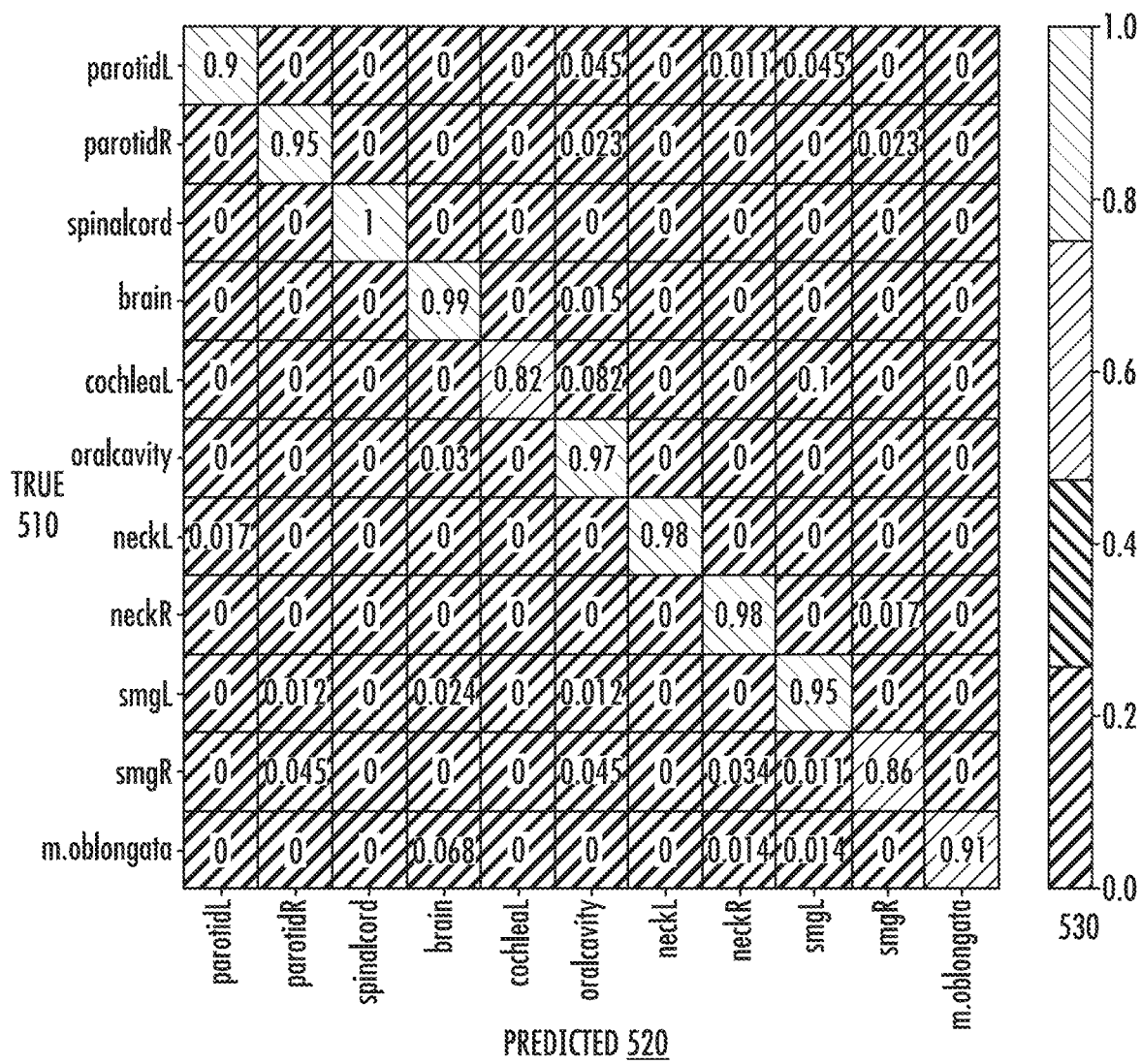
FIG. 5 is a block diagram of a confusion matrix for classification showing performance of the 3D ResNet model of FIG. 4, according to an embodiment.

A non-limiting example of the invention is illustrated in FIGS. 4 and 5 as well as Table 1. FIG. 4 and Table 1 show a residual neural network 400 applied as a machine learning classifier for segmentations predictions of head and neck (H&N) OARs. The classifier 400 incorporates a 3D residual neural network 400 (3D ResNet) with ten residual blocks 450, as shown in the 3D ResNet specification of Table 1. A ResNet is a convolutional neural network (CNN) that builds on constructs based on pyramidal cells in the cerebral cortex. 3D ResNet 400 utilizes residual connections for "identity mapping," which adds the output from the previous layer to the layer ahead. For example, residual connection 430 skips over layers 410 and 420 and causes inputs x and F(x) to be combined as input to the next layer. ResNet models may be implemented with double-layer or triple-layer residual connections that contain nonlinearities (ReLu 440). Residual blocks and pooling layers of ResNet classifier 400 can down sample input variables to an output vector shaped according to a number of target classes, e.g., 11 H&N classes (FIG. 5). 3D ResNet 400 includes a total of 129,291 layer parameters, of which 128,859 were trainable parameters and 432 were non trainable parameters.

TABLE 1

3D ResNet Specification

| Layer (type) | Output Shape | Parameter # |
| --- | --- | --- |
| input_1 (InputLayer) | (None, 48, 48, 48, 1) | 0 |
| conv3d (Conv3D) | (None, 24, 24, 24, 8) | 2752 |
| batch_normalization (BatchNo) | (None, 24, 24, 24, 8) | 32 |
| dropout (Dropout) | (None, 24, 24, 24, 8) | 0 |
| re_lu (ReLU) | (None, 24, 24, 24, 8) | 0 |
| resnet_block (resnet_block) | (None, 24, 24, 24, 8) | 1768 |
| resnet_block_1 (resnet_block) | (None, 24, 24, 24, 8) | 1768 |
| resnet_block_2 (resnet_block) | (None, 12, 12, 12, 16) | 3680 |
| resnet_block_3 (resnet_block) | (None, 12, 12, 12, 16) | 6992 |
| resnet_block_4 (resnet_block) | (None, 12, 12, 12, 16) | 6992 |
| resnet_block_5 (resnet_block) | (None, 12, 12, 12, 16) | 6992 |
| resnet_block_6 (resnet_block) | (None, 6, 6, 6, 32) | 14528 |
| resnet_block_7 (resnet_block) | (None, 6, 6, 6, 32) | 27808 |
| resnet_block_8 (resnet_block) | (None, 6, 6, 6, 32) | 27808 |
| resnet_block_9 (resnet_block) | (None, 6, 6, 6, 32) | 27808 |
| global_average_pooling3d (Gl) | (None, 32) | 0 |
| dense2 (Dense) | (None, 11) | 363 |

Training data for the H&N classifier inputted 11 OAR medical images from the Cancer Imaging Archive, reference: Wee, L., & Dekker, A. (2019). Data from Head-Neck-Radiomics-HN1 [Data set], https://doi.org/10.7937/tcia.2019.8kap372n The Cancer Imaging Archive. The Cancer Imaging Archive is a service funded by the National Cancer Institute's Cancer Imaging Program and operated by the University of Arkansas for Medical Sciences that de-identifies and hosts a large open-access database of medical images for cancer. In pre-processing the training data, OAR medical images were cropped to an enclosing cube, and were re-sized to a normalized size of 48×48×48 voxels. Data augmentation pre-processing rotated the normalized volumes ±20° about 1, 2, or 3 axes. In a curated selection of OARs training data, the machine learning classifier was trained on 20 of each OAR, 220 total. 80% of this data was used in training and 20% was used in model validation. Model validation included an increase of learning iterations over the full training data set (e.g., 100-200 epochs), which may help to improve performance in the validation set.

At inference time, model training incorporated about 900 OARs in training and validation data in determining shape distribution of the H&N OARs. A series of iterative model runs processed parameters of convolutional layers and performed dimensionality reduction on input variables to generate information on the weights of various convolutional layers. Dimensionality reduction employed PCA and t-SNE techniques to generate two-dimensional and three-dimensional plots in which each patient's OAR is a point. These plots revealed clusters and outliers in the OAR data to support unsupervised machine learning algorithms and clustering analysis of the data, and to aid in visualizing shape distribution of the H&N OARs.

FIG. 5 shows a confusion matrix for a machine learning classifier depicting performance of the 3D ResNet model 400. Confusion matrix 500 includes 11 categories or classes corresponding to a set of organs or anatomical regions to be identified by the H&N machine learning classifier for each of the segmentations input into the model. These classes include left parotid (abbreviated parotidL in the figure), right parotid (parotidR), spinal cord, brain, left cochlea (cochlea), oral cavity, left neck (neckL), right neck (neckR), left submandibular gland (smgL), right submandibular gland (smgR), and medulla oblongata (m.oblangata). Each row of the matrix represents the instances in an actual class, True 510. Each column represents the instances in a predicted class, Predicted 520.

At each row of confusion matrix 500, respective cells show the decimal value of respective instances of predicted class that correspond to the actual class. For example, for actual class m.oblangata the predicted class m.oblangata has a decimal value of 0.91, representing the proportion of correct predictions. The predicted class brain has a decimal value of 0.068, the predicted class neckR has a decimal value of 0.014, the predicted class smgL has a decimal value of 0.014, and other predicted classes have a decimal value of 0.0. A color gradient or grayscale gradient 530 and corresponding color coding of the matrix cells aid in visualizing proportions of correct predictions and incorrect predictions by the classifier.

Figure 6:
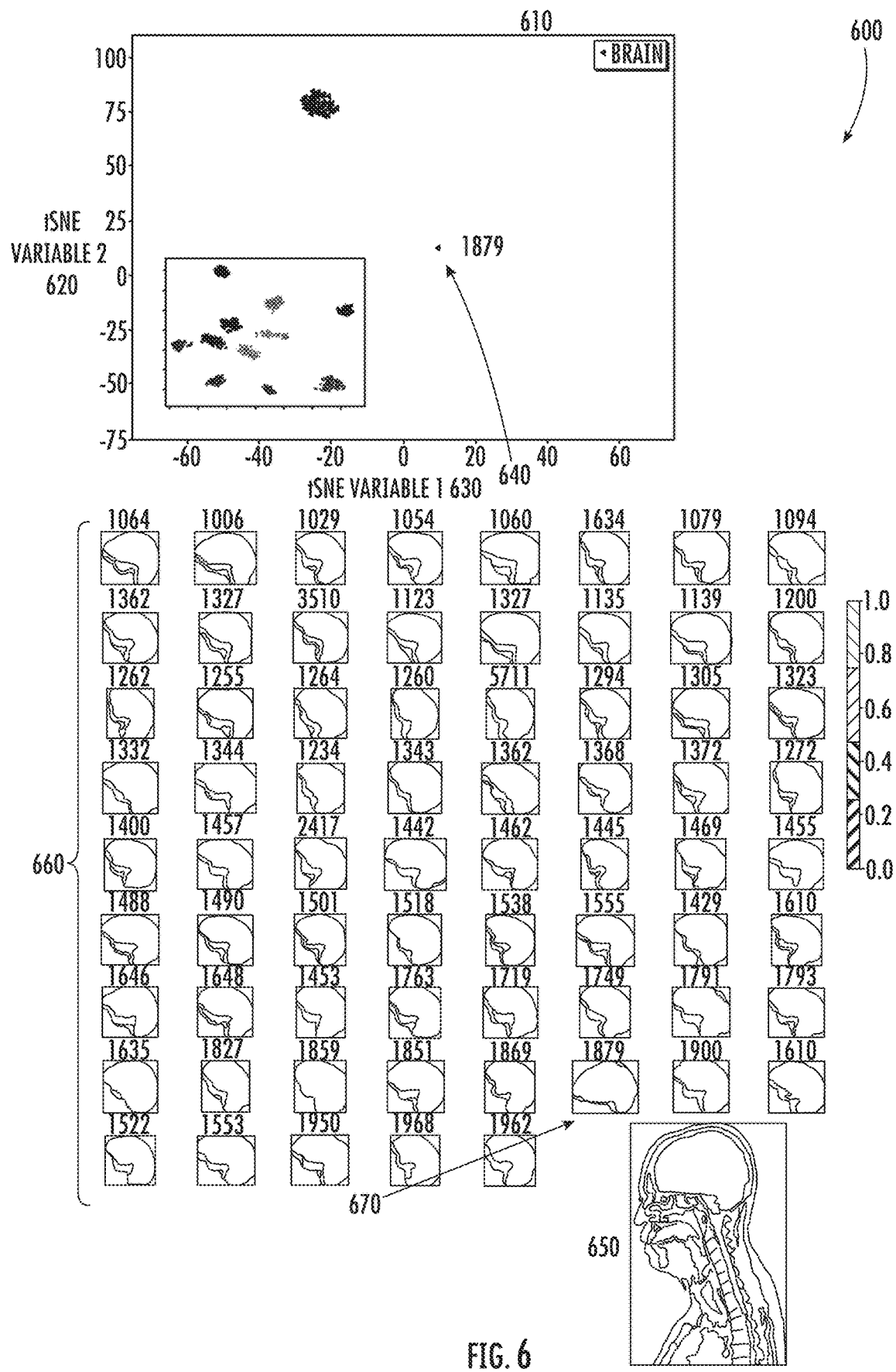
FIG. 6 illustrates a set of model contour segmentations and a two-dimensional t-SNE plot for a brain, according to an embodiment.

Non-limiting examples of the invention as applied to various organs of interest are illustrated in FIGS. 6-10. FIGS. 6-10 show model contour segmentations and two-dimensional t-SNE plots for various H&N organs and anatomical regions generated via the 3D ResNet deep learning model of FIG. 4. FIG. 6 shows at 600 a set of model contour segmentations and two-dimensional t-SNE plot for brain. The model processes a set of model contour segmentations of sagittal view of brain with voxel values summed, shown in indexed images 660. Model contour segmentations are generated from respective patient images, e.g., image 650. For each patient image, weights from the 3D ResNet model are extracted and the model applies dimensionality reduction to generate a two-dimensional t-SNE plot 610 of t-SNE variable2 620 against t-SNE variable1 630. T-SNE plot 610, in which each point corresponds to one of the model contour segmentations, displays clusters and an outlier point 640. Outlier 640 corresponds to model contour segmentation 670, index no. 1879.

Figure 7:
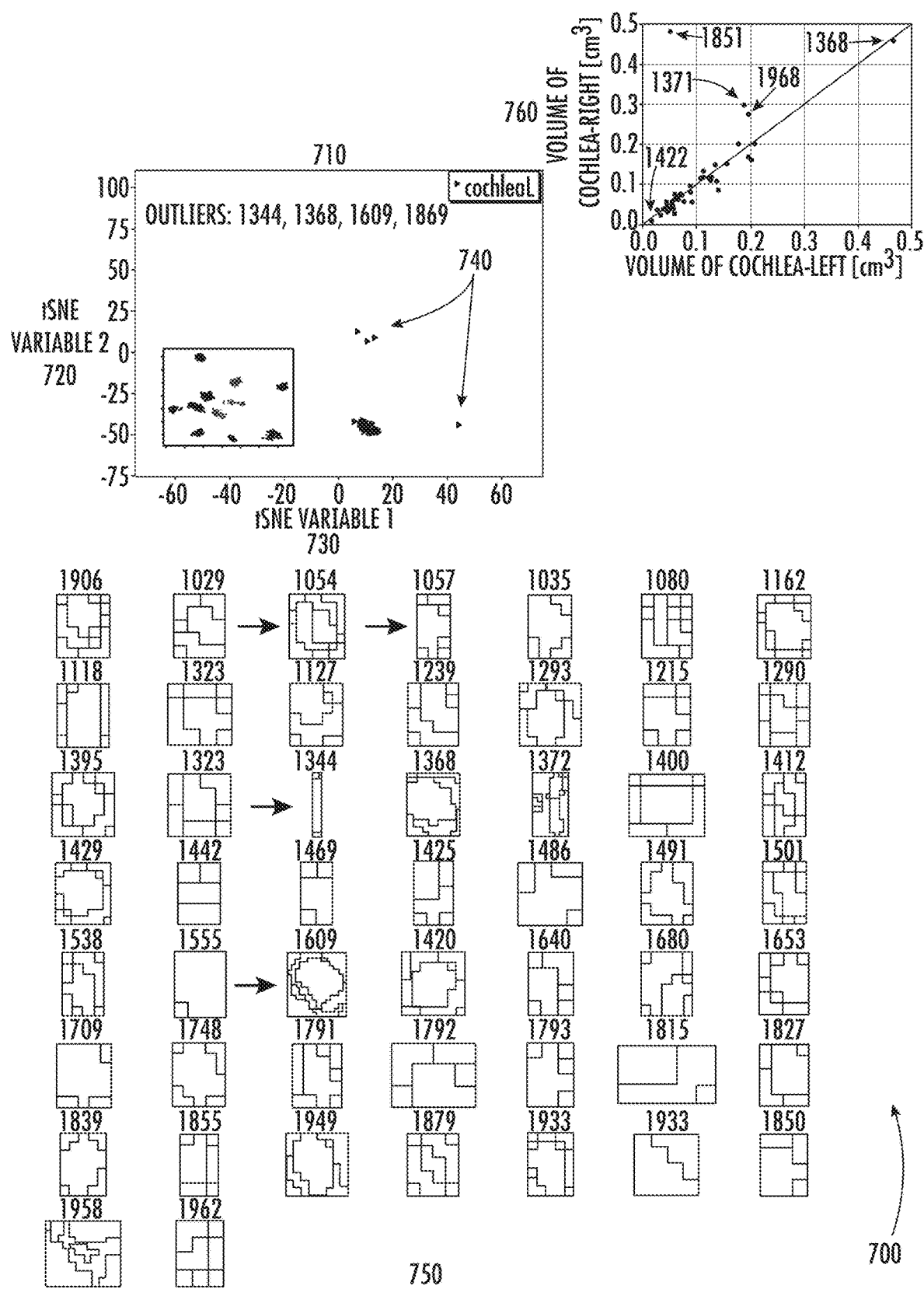
FIG. 7 illustrates a set of model contour segmentations and a two-dimensional t-SNE plot for a left cochlea, according to an embodiment.

FIG. 7 shows at 700 a set of model contour segmentations and a two-dimensional t-SNE plot for a left cochlea. The 3D ResNet model processes a set of model contour segmentations of left cochlea, shown in the array of indexed images 750. Model contour segmentations are generated from respective patient images. For each segmentation, weights from the 3D ResNet model are extracted and the model applied dimensionality reduction to generate a two-dimensional t-SNE plot 710 of t-SNE variable2 720 against t-SNE variable1 730. T-SNE plot 710, in which each point corresponds to one of the model contour segmentations, displays clusters and four outlier points 740. Outlier points 740 corresponds to model contour segmentations indicated by arrows in the array 750, index nos. 1344, 1368, 1609, 1869. The 3D ResNet model also generated a distribution plot 760 of volume of Cochlea-Left against volume of Cochlea-Right. Plot 760 shows a cluster of patient images with very similar volume, and patient image outliers in which Cochlea-Right had a significantly larger volume than Cochlea-Left.

Figure 8:
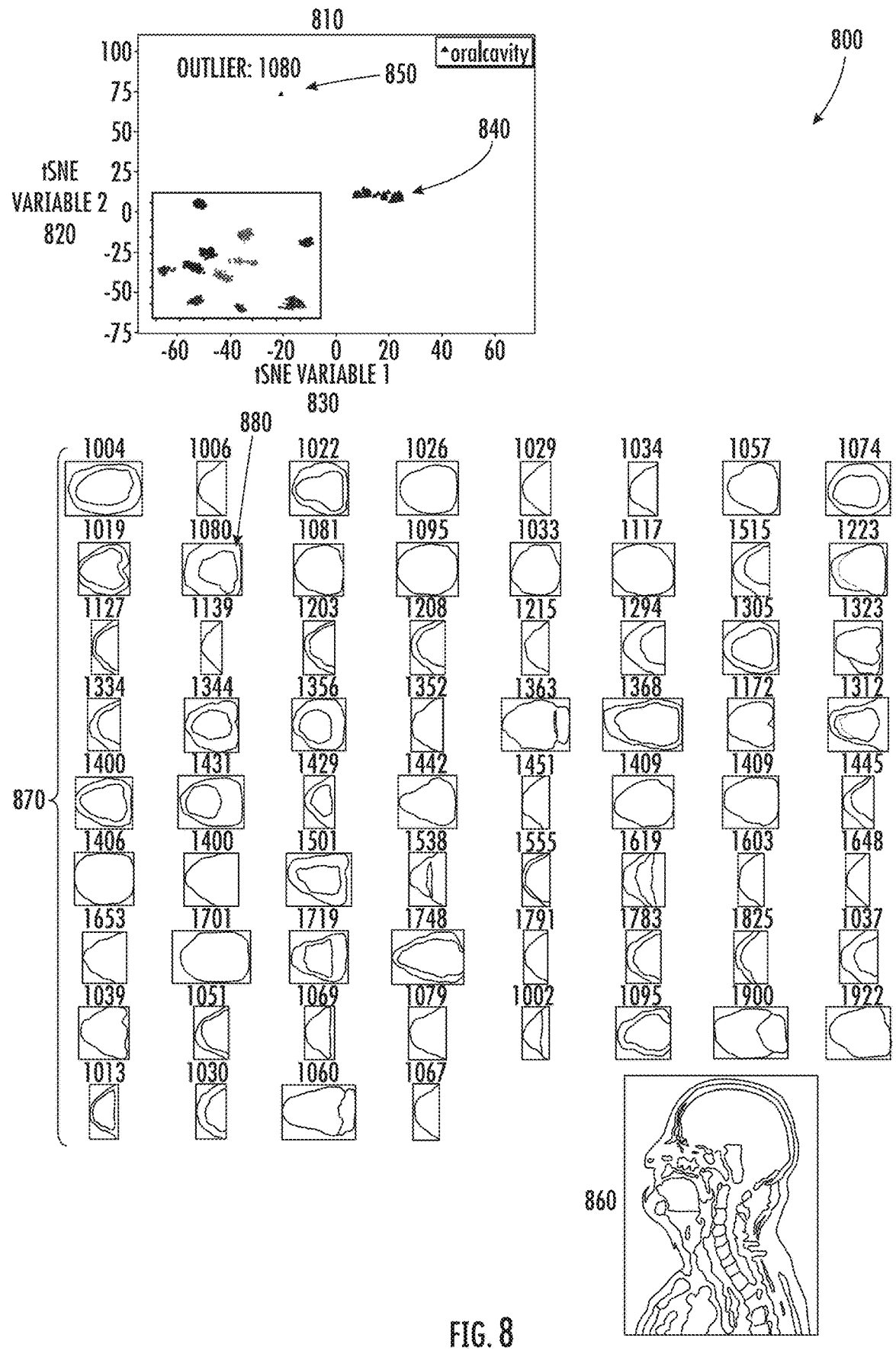
FIG. 8 illustrates a set of model contour segmentations and a two-dimensional t-SNE plot for an oral cavity, according to an embodiment.

FIG. 8 shows at 800 a set of model contour segmentations and a two-dimensional t-SNE plot for oral cavity. The 3D ResNet model processes a set of model contour segmentations of oral cavity, shown in indexed images 870. Model contour segmentations are generated from respective patient images, e.g., image 860. For each segmentation, weights from the 3D ResNet model are extracted and the model applied dimensionality reduction to generate a two-dimen-sional t-SNE plot 810 of t-SNE variable 2 820 against t-SNE variable1 830. T-SNE plot 810, in which each point corresponds to one of the model contour segmentations, displays several clusters 840 and an outlier point 850. Outlier 850 corresponds to model contour segmentation 880, index no. 1080.

Figure 9:
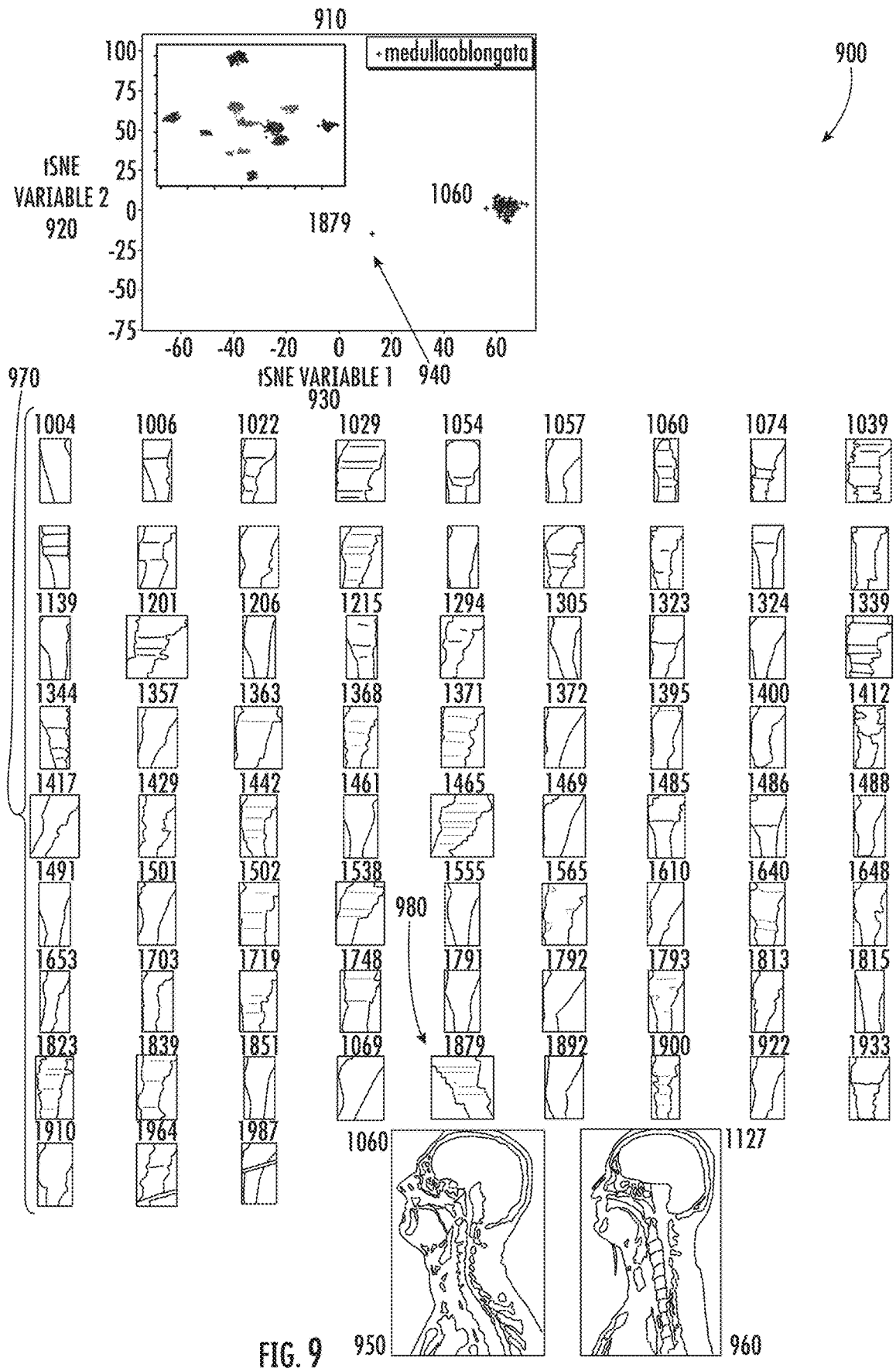
FIG. 9 illustrates a set of model contour segmentations and a two-dimensional t-SNE plot for medulla oblongata, according to an embodiment.

FIG. 9 shows a set of model contour segmentations and a two-dimensional t-SNE plot for medulla oblongata. The 3D ResNet model processes a set of model contour segmentations of medulla oblongata (ResNet block 7), shown in indexed images 970. Model contour segmentations are generated from respective patient images, e.g., images 950, 960. For each segmentation, weights from the 3D ResNet model are extracted and the model applied dimensionality reduction to generate a two-dimensional t-SNE plot 910 of t-SNE variable2 920 against t-SNE variable 1 930. T-SNE plot 910, in which each point corresponds to one of the model contour segmentations, displays an outlier point 940. Outlier 940 corresponds to model contour segmentation 980, index no. 1879.

Figure 10:
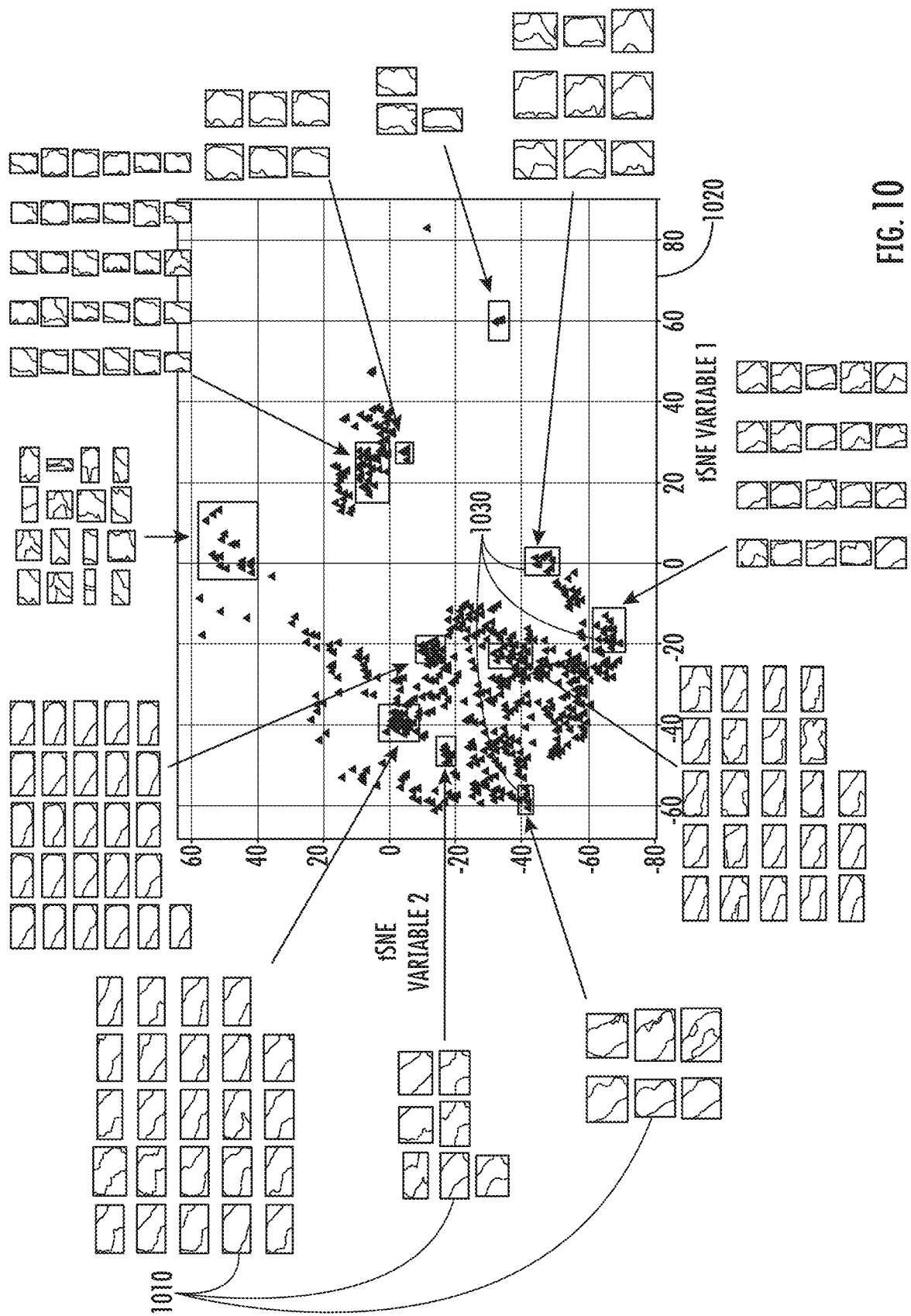
FIG. 10 illustrates a set of model contour segmentations and a two-dimensional t-SNE plot for a uterus, according to an embodiment.

FIG. 10 shows a set of model contour segmentations and a two-dimensional t-SNE plot for a uterus. Model contour segmentations 1010 are generated from respective patient images. For each segmentation, weights from the 3D ResNet model are extracted and the model applied dimensionality reduction to generate a two-dimensional t-SNE plot 1020 of t-SNE variable2 against t-SNE variable1. T-SNE plot 1020, in which each point corresponds to one of the model contour segmentations, displays clusters 1030. FIG. 10 maps various clusters 1030 in t-SNE plot 1020 against corresponding subsets of the set of model contour segmentations 1010.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What I claim is:

1. A method comprising:
   receiving, by the processor, a second image comprising a first overlay predicting a segmentation of an organ of a patient, wherein the first overlay is generated by a first machine learning model using a first image depicting an anatomical region of the patient including the organ; and
   executing, by the processor, a second machine learning model that receives the second image to classify similarity between the second image and a set of third images representing a set of second structures by characterizing the extent to which the second image is drawn from a distribution of images in a plurality of images within the set of third images;
   wherein the set of third images representing the set of second structures is used to train the second machine learning model.

2. The method of claim 1, wherein the second machine learning model is configured to identify at least one cluster of second structures represented by the set of third images.

3. The method of claim 2, wherein the distribution of images in the plurality of images comprises a distribution of images of at least one cluster of second structures represented by the set of third images.

4. The method of claim 2, wherein the second machine learning model is further configured to identify at least one outlier second structure within the set of second structures represented by the set of third images.

5. The method of claim 1, wherein the second machine learning model is configured to classify the similarity between the second image and the set of third images representing the set of second structures by indicating whether or not the second image is drawn from the same distribution of images as the plurality of images within the set of third images.

6. The method of claim 5, further comprising displaying, by the processor, the classifying the similarity between the second image and the set of third images representing the set of second structures by indicating whether or not a contour of the second image is drawn from the same distribution of contours as the plurality of images within the set of third images.

7. The method of claim 5, in the event of classifying the second image as not drawn from the same distribution of images as the plurality of images within the set of third images, further comprising displaying, by the processor, an attribute of a patient associated with the classification.

8. The method of claim 5, in the event of classifying the second image as not drawn from the same distribution of images as the plurality of images within the set of third images, further comprising transmitting, by the processor, a notification instructing a manual review of the second image.

9. The method of claim 1, wherein the second machine learning model is a deep learning model comprising one or more of neural networks, convolutional neural networks, residual neural networks, random forest, and support vector machines.

10. The method of claim 1, wherein the second machine learning model is configured to perform dimensional reduction on model inputs via one or both of principal component analysis (PCA) and t-distributed stochastic neighbor embedding (t-SNE).

11. The method of claim 1, further comprising receiving, by the processor, the first image depicting an anatomical region of the patient including the organ.

12. The method of claim 1, wherein the first image is one or more of an X-ray image, computed tomography (CT) image, magnetic resonance imaging (MRI) image, positron emission tomography (PET) image, or ultrasound image.

13. The method of claim 1, wherein the second machine learning model is configured to generate one or more of a one-dimensional plot in which each of the second structures of the set of third images is represented by a respective point, a two-dimensional plot in which each of the second structures of the set of third images is represented by a respective point, and a three-dimensional plot in which each of the second structures of the set of third images is represented by a respective point.

14. A method comprising:
receiving, by the processor, a second image comprising a first overlay predicting a segmentation of an organ of a patient, wherein the first overlay is generated by a first machine learning model using a first image depicting an anatomical region of the patient including the organ; and executing, by the processor, a second machine learning model that receives the second image to classify the second image as one of a predefined set of class names, and to classify similarity between the second image and a set of third images, wherein the set of third images represent segmentations of organs of prior patients of the same class name as the second image, wherein a set of fourth images represent segmentations of organs of prior patients of a different class name than the second image, wherein the set of third images and the set of fourth images are used to train the second machine learning model.

15. The method of claim 14, wherein the predefined set of class names represents a curated selection of organs based upon an anatomy of interest.

16. A system comprising:
a server comprising a processor and a non-transitory computer-readable medium containing instructions that when executed by the processor causes the processor to perform operations comprising:

receive a second image comprising a first overlay predicting a segmentation of an organ of a patient, wherein the first overlay is generated by a first machine learning model using a first image depicting an anatomical region of the patient including the organ; and execute a second machine learning model that receives the second image to classify similarity between the second image and a set of third images representing a set of second structures by characterizing the extent to which the second image is drawn from a distribution of images in a plurality of images within the set of third images;

wherein the set of third images representing the set of second structures is used to train the second machine learning model.

17. The system of claim 16, wherein the processor is further configured to perform operations comprising:

identify at least one cluster of second structures represented by the set of third images, wherein the distribution of images in the plurality of images comprises a distribution of images of at least one cluster of second structures represented by the set of third images.

18. The system according to claim 16, wherein the processor is further configured to perform operations comprising:

classify the similarity between the second image and the set of third images representing the set of second structures by indicating whether or not the second image is drawn from the same distribution of images as the plurality of images within the set of third images; and in the event of classifying the second image as not drawn from the same distribution of images as the plurality of images within the set of third images, further comprising transmitting, by the processor, a notification instructing a manual review of the second image.

19. The system according to claim 16, wherein the second machine learning model is a deep learning model comprising one or more of neural networks, convolutional neural networks, residual neural networks, random forest, and support vector machines; wherein the second machine learning model is trained via an unsupervised training protocol.

20. The system according to claim 16, wherein the processor is further configured to perform operations comprising:

execute the second machine learning model that receives the second image to classify the second image as one of a predefined set of class names, and to classify similarity between the second image and a set of third images, wherein the set of third images represent segmentations of organs of prior patients of the same class name as the second image, wherein a set of fourth images represent segmentations of organs of prior patients of a different class name than the second image, wherein the set of third images and the set of fourth images are used to train the second machine learning model.

* * * * *